US00PP34599P2

(12) United States Plant Patent
Ruter

(10) Patent No.: US PP34,599 P2
(45) Date of Patent: Sep. 20, 2022

(54) ***HIBISCUS* PLANT NAMED 'RUTHIB4'**

(50) Latin Name: *Hibiscus moscheutos*
Varietal Denomination: 'RutHib4'

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 4 days.

(21) Appl. No.: 17/377,871

(22) Filed: Jul. 16, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Thomas Horstemeyer, LLP

(57) ABSTRACT

A new and distinct cultivar of *Hibiscus* plant named 'RutHib4' is characterized by a combination of compact, dense growth form, that is smaller than either parent, bright red flowers with a darker red eyespot, better adaptation to southern climates, and improved disease resistance to aerial phytophthora, fungal and bacterial leaf spots.

6 Drawing Sheets

Botanical designation: *Hibiscus moscheutos.*
Cultivar denomination 'RutHib4'.

BACKGROUND OF THE INVENTION

The present invention relates to a new and distinct cultivar of *Hibiscus*, botanically know as *Hibiscus moscheutos*, and hereinafter referred to by the cultivar name 'RutHib4'.

The new *Hibiscus moscheutos* 'RutHib4' is a product of a planned breeding program conducted by the inventors at a horticulture farm in Watkinsville, Ga. The objective of the *Hibiscus* breeding is to create new plant cultivars with ornamental leaf distinctions, abundant flowers, and tolerance to insects and pathogens. These and other qualities are enumerated herein.

The new *Hibiscus moscheutos* 'RutHib4' is a product of *Hibiscus moscheutos* 'RutHib2' (U.S. Plant Pat. No. 30,853) x *Hibiscus moscheutos* 'Midnight Marvel' (U.S. Plant Pat. No. 24,079). The cross was made in 2013. 'RutHib4' has been evaluated through trials at a horticulture farm in Watkinsville, Ga. from spring of 2014, and the plant 'RutHib4' was selected in 2014.

Asexual reproduction of the new *Hibiscus moscheutos* 'RutHib4' using vegetative terminal cuttings in controlled environment has been continued in Watkinsville, Ga. since 2014, and in Pennsylvania since 2015. Observations of the resulting 'RutHib4' progeny have shown that the unique features of this new *Hibiscus moscheutos* 'RutHib4' are stable and reproduced true to type in successive generations.

SUMMARY OF THE INVENTION

The new *Hibiscus* cultivar 'RutHib4' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Hibiscus moscheutos* cultivar named 'RutHib4'. In combination, these traits set 'RutHib4' apart from all other existing varieties of *Hibiscus* known to the inventors.

1. Compact, dense growth form, smaller than either parent;
2. Bright red flowers with a darker red eyespot;
3. Better adaptation to southern climates than 'Midnight Marvel' or 'Mars Madness' (U.S. Plant Pat. No. 27,838);
4. Improved disease resistance to aerial phytophthora, fungal and bacterial leaf spots than some other *Hibiscus*, such as 'Midnight Marvel' or 'Mars Madness'.

Specifically, plants of the new *Hibiscus* differ from the closest related cultivars, including the female parent *H. moscheutos* 'RutHib2' and the male parent *H. moscheutos* 'Midnight Marvel' (U.S. Plant Pat. No. 24,079) as well as similar cultivar 'Mars Madness' (U.S. Plant Pat. No. 27,838), in at least the following characteristics:

1. Plants of the new *Hibiscus* exhibit a smaller, more compact growth form than either parent;
2. Plants of the new *Hibiscus* are more resistant to aerial phytophtora and more suitable for growth in southern climates than the male parent 'Midnight Marvel' or 'Mars Madness', which were unable to survive in the field for more than three seasons in Georgia;
3. Plants of the new *Hibiscus* are smaller in stature and have a different flower color compared to 'RutHib2' or 'Mars Madness'.

BRIEF DESCRIPTION OF THE PHOTOGRAPHS

The accompanying colored photographic illustrations show the overall appearance and distinct characteristics of the new cultivar of *Hibiscus moscheutos* 'RutHib4' showing the colors as true as possible. Colors in the photographs may differ slightly from the color values cited in the detailed botanical description, which accurately describes the colors of the new *Hibiscus moscheutos* 'RutHib4'. The photographs were taken of plants grown outdoors in West Grove, Pa. on during Summer 2020.

The photographs labeled FIG. 1A and FIG. 1B depict close up views of a typical flower of the new *Hibiscus moscheutos* 'RutHib4' plant in different lighting, showing the bright red coloring, deep red eyespot and green foliage.

The photograph labeled FIG. 2 depicts a more distant view of a typical three-year-old summer 'RutHib4' plant growing alongside other *Hibiscus* plants of different form and color, illustrating the bright red coloring and compact form of the 'RutHib4' cultivar.

Figure 1A:
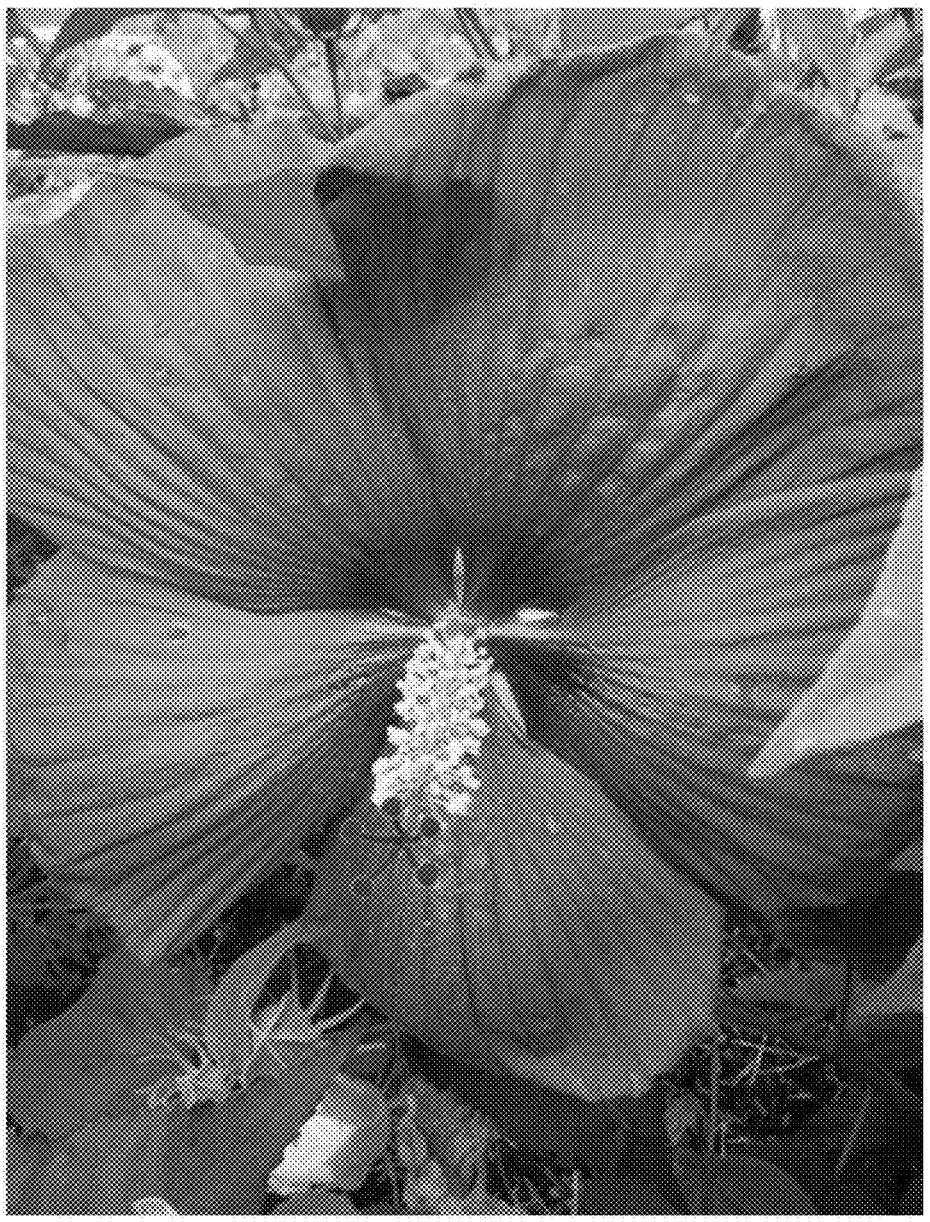
Figure 1B:
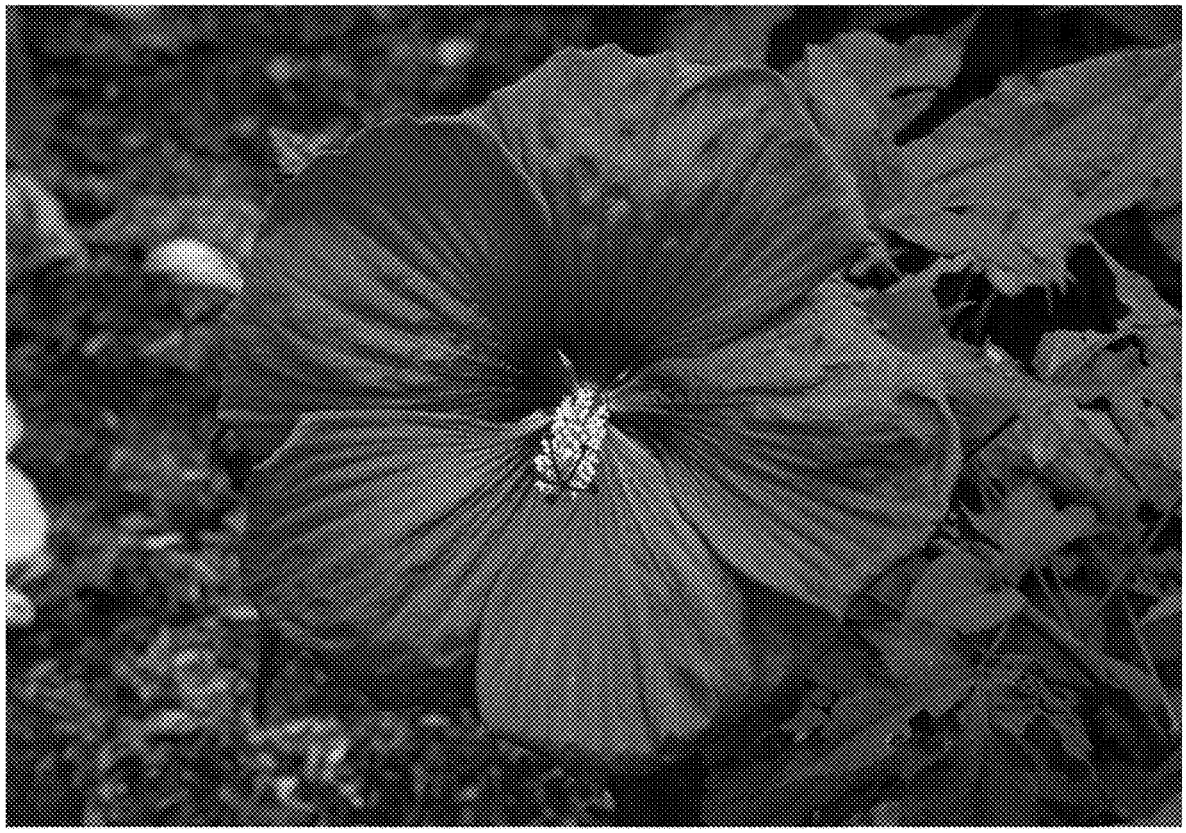
Figure 2:
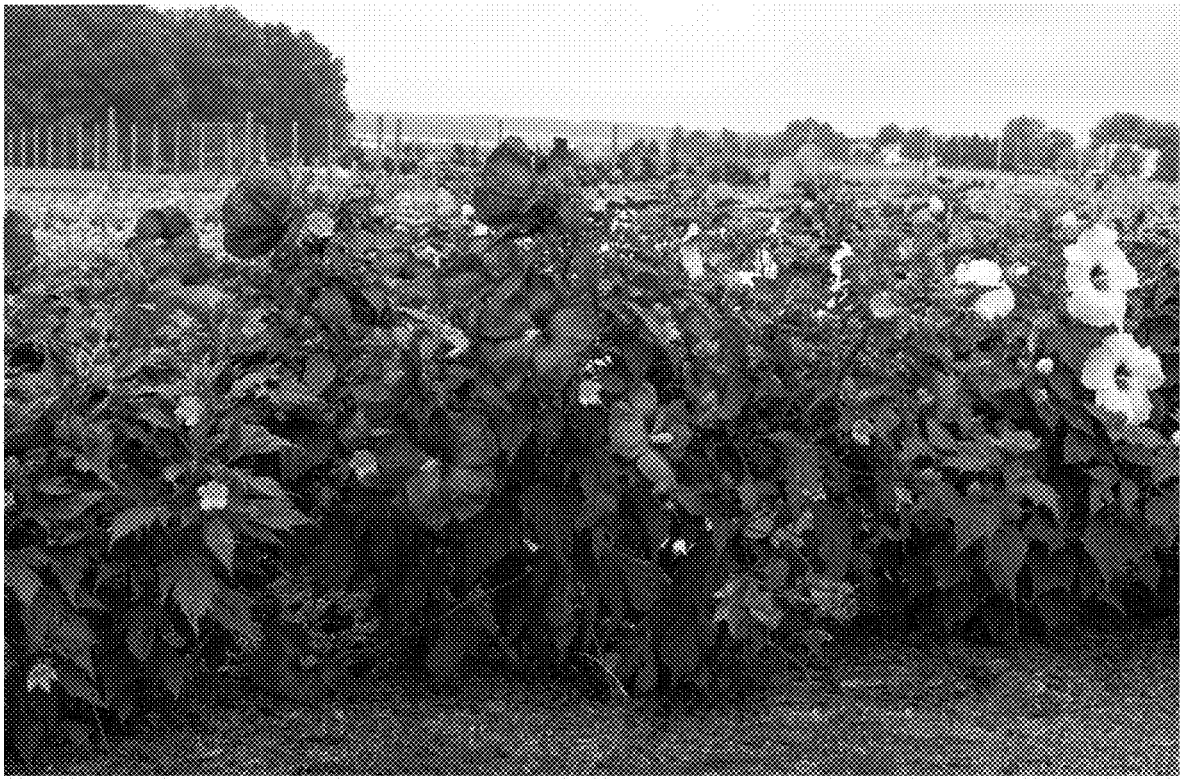
Figure 3:
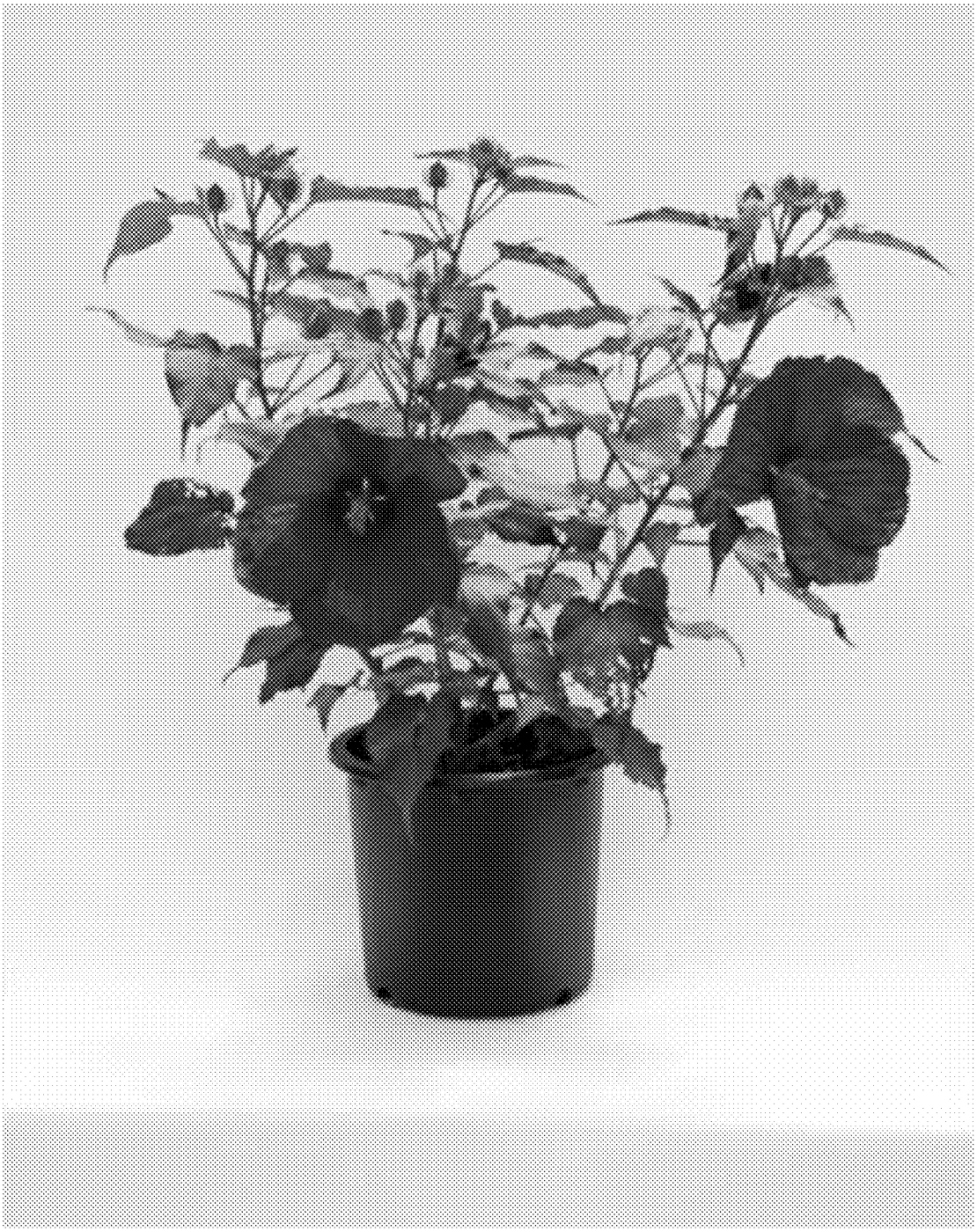
FIG. 3 is a photograph of a typical (2-year-old) *Hibiscus moscheutos* 'RutHib4' potted plant showing its form and bright red flowers.
Figure 4:
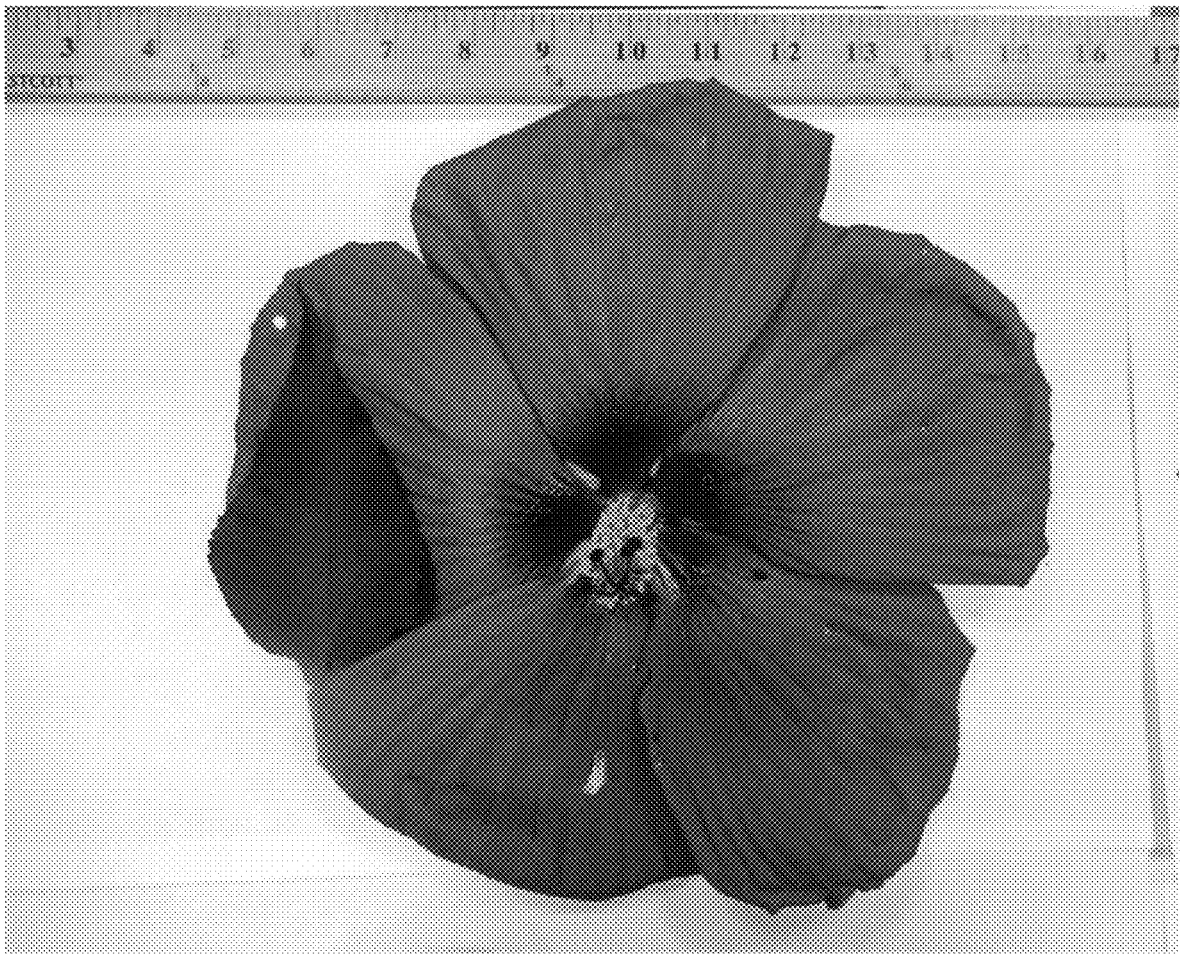
FIG. 4 is a close-up photograph of a flower and leaf of the "RutHib4' photograph with a ruler to show the size and coloring of a typical flower and leaf of the new *Hibiscus*.
Figure 5:
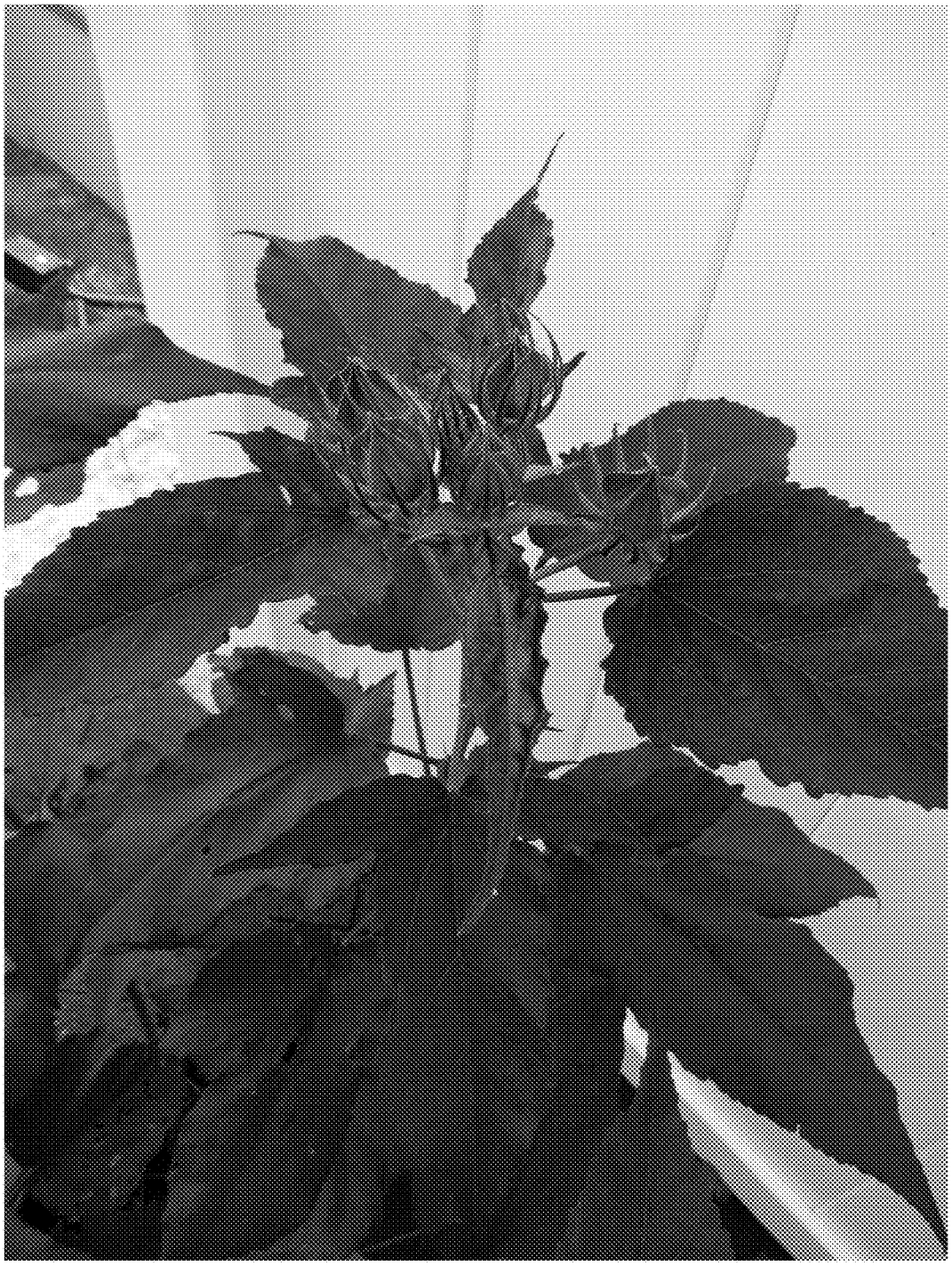

The photograph labeled FIG. 5 depicts a typical *Hibiscus moscheutos* 'RutHib4' prior to bloom, showing buds and the deep purple-green foliage.

DETAILED BOTANICAL DESCRIPTION

The following traits have been consistently observed in the original plant of this new variety and in asexually propagated progeny grown from vegetative cuttings in Watkinsville, Ga., and West Grove, Pa., and, to the best knowledge of the inventors, their combination forms the unique characteristics of the new variety 'RutHib4'.

Throughout this specification, color names beginning with a small letter signify that the name of that color, as used in common speech, is aptly descriptive. Color names beginning with a capital letter designate values based upon The R.H.S. Colour Chart, $6^{th}$ edition published by The Royal Horticultural Society, London, England in 2015, except where general terms of ordinary dictionary significance are used.

The aforementioned photographs and following observations, measurements, and values describe plants of the *Hibiscus moscheutos* cultivar named 'RutHib4'. Data were collected from 2-year old field plants grown outdoors and planted in the ground on a horticulture farm and nursery in West Grove, Pa. with no trims. The average low temperatures ranged from about 0° F. to 5° F. in the winter and about 48° F. to 84° F. in summer. The data below were collected in the month of August of 2020.

Botanical classification: *Hibiscus moscheutos* 'RutHib4'.

Commercial classification: Ornamental shrub.

Parentage: *Hibiscus moscheutos* 'RutHib2' (U.S. Plant Pat. No. 30,853) x *Hibiscus moscheutos* 'Midnight Marvel' (U.S. Plant Pat. No. 24,079).

Growth and propagation:

*Propagation type*.—Vegetative terminal cutting.

*Growth rate*.—Root initiation — 2 weeks, rooted liners in 4-6 weeks before or after flowering.

*Root description*.—Fleshy, branching and dense.

Plant description:

*Form*.—Hardy herbaceous shrub, vibrant red flowers, blooms from July to November in Southeastern, PA and from mid-June until October in Georgia.

*Habit*.—Upright, spreading, mounding, with 10 to 12 thick upright and heavily branched main stems producing a upright spreading mound to about 104 cm tall and about 132.3 cm wide, widest about 64 cm above soil line; 12 to 16 primary branches per main stem protruding at about 80° from horizontal for lowest branches to about 45° angle from horizontal for distal branches, flowering from base to top of plant with about 20 to 28 flowers per main stem.

*Usage*.—Various uses, such as container patio plants, potted plants, landscape use such as border, hedge, and mass planting.

*Vigor*.—Moderate.

*Size of plant*.—A. Height: up to about 104 cm in PA (planted in ground in GA on May 26, 2021 with a height of about 50 cm, as compared to the height of 'RutHib2' in GA of about 75 cm and 'Midnight Marvel' or 'Mars Madness', which did not survive in GA). B. Plant diameter and area of spread (diameter of the canopy): up to about 132 cm in PA (planted in ground in GA on May 26, 2021 with a width of about 75 cm, as compared to the width of RutHib2 in GA of about 110 cm and 'Midnight Marvel' or 'Mars Madness', which did not survive in GA).

*Stem*.—A. Color (RHS): 1. Main Stem: Base: greyed-red 182B; distal portion: between RHS 183A and RHS 187C. 2. Lateral Branches: Between RHS 176A and RHS 144C. B. Length: main stem, about 102.0-104 cm; lateral branches, about 31.2 cm. C. Diameter: base, about 3.8 cm; lateral branches, about 5.0 mm. D. Pubescence: none; glabrous. E. Shape: Terete. F: Odor (of bruised stem): none detected. G: Description: glaucous. H: Strength: non-lodging.

*Internode*.—A. Number: about 30 nodes per stem below flowers, average internode length about 4.0 cm of unpinched plant below flower and average about 2.0 cm in upper flowering section without branches, largest in middle portion of stem. B. Color: Varying with light exposure, same as surrounding stem.

*Leaf*.—A. Mature size (L×W): About 14.0 cm×about 9.5 cm, becoming smaller distally. B. Arrangement on stem: alternate. C. Leaf number: single. D. Color (RHS): Adaxial color nearest to Yellow-Green147A with purple spots of nearest RHS 187A showing; abaxial color nearest RHS 147B. 1. Fall-Winter: fall color if present Greyed-Orange 167B, deciduous. 2. Spring-Summer: as per above. E. Apex: attenuate; Base: rounded. F. Margin: dentate. G. Shape: deeply cleft to slightly lobed; lobing is shallow to medium. H. Number of lobes: mostly three-lobed with some five-lobed. I. Pubescence: glaucous. J. Venation: Palmate; lustrous; ridged on abaxial. K. Vein color: Adaxial proximally nearest RHS Greyed-Red 187B and progressing to nearest RHS 187A distally; abaxial nearest RHS 186B. L. Texture: glabrous, lustrous adaxial center, dull adaxial sides and below. M. Odor when crushed: none detected.

*Petiole*.—A. Length: about 6.5 cm to about 7.5 cm. B. Shape: mostly terete, slightly flattened at base. C. Color (RHS): Adaxial between RHS Greyed-Red 183B and RHS Red-Purple 59A; abaxial between RHS 182B. D. Pubescence: glaucous. E. Diameter: about 4.0 mm-5.0 mm. F. Texture: glabrous.

*Inflorescence(s)*.—A. Type: Solitary. B. Number per Plant: about 10 average/plant at one time; C. Size (L×W): about 12 cm×12 cm. D. Color (RHS): 184A. E. Longevity: 1-2 days. F. Peduncle. 1. Length: about 3.5 cm. 2. Diameter: about 4.0 cm. 3. Color (RHS): 145A. 4. Surface Texture: smooth. 5. Strength: strong. 6. Aspect: about 30 degrees.

*Flower*.—A. Number per Inflorescence: about 3-5 per stem in a cluster. B. Axillary or Terminal: axillary, single. C. Symmetry: radial. D. Size: height, about 7.0 cm; diameter, about 23.0 cm. E. Pubescence/Texture: glabrous. F. Flower form/profile: form is large, whirled, and conspicuous; profile is large and flat with protruding reproductive parts. G. Color at peak bloom (RHS): 1. Upper surface: Red 184A with 187B eye. 2. Lower surface: 184A. H. Fragrance: none detected. I. Duration: approximately 2 days on the plant. J. Time range for showiness: blooms from July to November in Southeastern, PA and from mid-June until October in Georgia. K. Bud: 1. Color (RHS): 185A when opening. 2. Shape: ovoid. 3. Length: about 5.5 cm. 4. Width: about 3.3 cm. L. Petals: 1. Number: 5. 2. Shape: Broadly obovate, overlapping on either side, palmately veined. 3. Size (l×w): about 12.0 cm×about 12 cm. 4. Apex: rounded, rippled. 5. Base: cuneate. 6. Margin: entire with moderate undulation. 7. Color at when first and fully opened (RHS): i. Upper surface: 184A with 187B eye. ii. Under surface: 184A. 8. Petal drop: Average. 9. Texture: smooth. 10. Arrangement: radial, actinomorphic. 11. Eye zone: present, about 2 cm in length (about ⅕-⅙ length of petal), small to medium compared to other varieties. 12. Eye zone extensions: absent. M. Epicalyx: 1. Margin: entire. 2. Texture: glabrous, dull surface abaxial and adaxial; 3. Shape: linear with sharply acute apex and attenuate base, arcuate upwards near calyx. 4. Number: 10-12 per flower. 5. Size: about 2.5 cm long tapering to base of about 3.0 mm wide. 6. Color: adaxial and abaxial color RHS 138A with abaxial tinting of nearest RHS 187C. N. Sepal(s): 1. Number: 5. 2. Size (l×w): about 3.5 cm×about 2.0 cm. 3. Apex: acute to aristate. 4. Base: fused to a cup shape in about 1.5 cm. 5. Margin: entire. 6. Texture: under surface puberulent. 7. Color at peak of bloom (RHS): a. Upper surface: 145A. b. Lower surfaces: 144B. O. Male reproductive structures (stamens): 1. Number: Approximately 180. 2. Staminal column length: 50-70 mm. 3. Anther: a. Size (l×w): about 2.0 mm×about 2.0 mm. b. Shape: reniform, dorsifixed. c. Color (RHS): 162B. d. Number: About 180. e. Texture/pubescence: smooth. 4. Filament: a. length: about 5.0 mm. b. Color (RHS): 51A. c. Texture: smooth. 5. Pollen: a. Quantity: numerous. b. Pollen color (RHS): 11B. P. Female Reproductive structures: 1. Pistil: a. Shape: enclosed in staminal column. b. Length: 5.5 cm. c. Position (superior, inferior, etc.): superior. d. Color (RHS): column 61C to 60B at the end tip. e. Pubescence: none. f. Arrangement: split in distal about 1.8 cm portion into 5 branches from column. g. Branch diameter: about 1.5 mm. 2. Stigma: a. Shape: round. b. Color (RHS): 53A. c. Diameter: about 4.0 mm. d. Pubescence: none. 3. Style: a. Length: 1.8 cm. b. Shape: interior to staminal column. c. Color (RHS): 53B. d. Pubescence: none. 4. Ovary: a. Shape: conical. b. Color (RHS): 187B. c. Pubescence: none.

*Fruit*.—A. Type: Loculicidal capsule; puberulent; globose, with abruptly acute apex. B. Size: 10.0 mm diameter. C. Depth: 1.0 cm. D. Shape: Start/Urn shaped. E. Color: 154 C. F. Surface texture: smooth.

*Seed*.—A. Description: Minutely floccose, typically globose. B. Size: about 4.0 mm in diameter. C. Color (RHS): between 158B and 158C. D. Count: about 50.

Weather/temperature tolerance: Plants of the new *Hibiscus* have been observed to tolerate temperatures from about −5° F. to about 100° F. and have been observed to be very tolerant to full sun, wet soils, mild drought, loam to clay soils conditions.

Disease/pest resistance: Plants of the new *Hibiscus* have been observed to be resistant to plants and pests common to *Hibiscus* such as, but not limited to, bacterial (Pseudomonas and Xanthomonas) and fungal leaf spots (Alternaria and Cercospora), aerial phytophthora.

It is claimed:

1. A new and distinct cultivar of the *Hibiscus* plant named 'RutHib4' as illustrated and described herein.

* * * * *